(12) United States Patent
Okuyama et al.

(10) Patent No.: US 7,488,472 B2
(45) Date of Patent: Feb. 10, 2009

(54) COSMETIC COMPOSITION FOR EYELASHES

(75) Inventors: Masaki Okuyama, Tokyo (JP); Masaki Kosugi, Tokyo (JP)

(73) Assignee: KOSE Corporation, Tokyo (JP)

(*) Notice: Subject to any disclaimer, the term of this patent is extended or adjusted under 35 U.S.C. 154(b) by 742 days.

(21) Appl. No.: 10/748,148

(22) Filed: Dec. 31, 2003

(65) Prior Publication Data

US 2004/0265257 A1  Dec. 30, 2004

(30) Foreign Application Priority Data

Jun. 26, 2003 (JP) ............................... 2003-183322

(51) Int. Cl.
  *A61Q 1/10* (2006.01)
(52) U.S. Cl. ...................................... 424/70.7; 424/401
(58) Field of Classification Search ........................ None
  See application file for complete search history.

(56) References Cited

U.S. PATENT DOCUMENTS 6,491,931 B1 * 12/2002 Collin ........................ 424/401

FOREIGN PATENT DOCUMENTS

| JP | 9-263518 | 10/1997 |
|---|---|---|
| JP | 11-106313 | 4/1999 |
| JP | 2001-31526 | 2/2001 |
| JP | 2001-278744 | 10/2001 |
| JP | 2002-154932 | 5/2002 |
| JP | 2002-284642 | * 10/2002 |

* cited by examiner

*Primary Examiner*—Jyothsna A Venkat
(74) *Attorney, Agent, or Firm*—Oblon, Spivak, McClelland, Maier & Neustadt, P.C.

(57) ABSTRACT

A cosmetic composition for eyelashes is disclosed which is excellent in make-up effects (long lash effect) such as making eyelashes appear longer and emphasizing eyes, and in long-lasting property of such make-up effects, exhibiting favorable usability, providing a uniform make-up film, and is also satisfactory in terms of stability. Provided is a cosmetic composition for eyelashes including: (A) polypropylene fibers having the thickness of 0.1 to 12 denier, and the length of 0.1 to 3 mm; and (B) an oil soluble resin.

22 Claims, No Drawings

COSMETIC COMPOSITION FOR EYELASHES

BACKGROUND OF THE INVENTION

1. Field of the Invention

The present invention relates to cosmetic compositions for eyelashes, which are excellent in make-up effects (long lash effect) such as making eyelashes appear longer and emphasizing eyes, and is excellent in long-lasting property of such effects, having favorable usability, providing a uniform make-up film, and also having satisfactory stability.

2. Description of the Related Art

Typical examples of conventional cosmetic compositions with fibers blended therein include cosmetic compositions for eyelashes. The cosmetic compositions for eyelashes have make-up effects such as highlighting of eyes by making the eyelashes curl upwards and appear thicker and longer.

Conventionally, these cosmetic compositions for eyelashes have been composed of solid oil contents, e.g., a wax, and powder, a film forming agent, a water soluble polymer and the like as principal components. In order to impart a variety of usability, feel during use and performances needed as a cosmetic composition, studies on various formulations, and blending of ingredients have been carried out. For example, in light of performances, there exist emulsified cosmetic compositions for eyelashes, having enhanced adhesiveness to the eyelashes through increasing the amount of a wax having a comparatively low melting point, a resin and various film forming agents to be blended. Accordingly, improved make-up effects such as thickening and highlighting of the eyelashes, or make-up effects such as emphasizing of the eyes by making the eyelashes fix as it is curled upwards can be achieved (for example, see, JP-A Nos. 11-106313 and 2001-31526). In addition, make-up effects such as highlighting of the application site can be also directed by blending fibers such as nylon and rayon to make the eyelashes appear longer (for example, see, JP-A Nos. 9-263518 and 2001-154932). Moreover, an attempt to produce appearances with deeply chiseled features has been also made by improving the color tone to emphasize the eyes (for example, see, JP-A No. 2001-278744).

SUMMARY OF THE INVENTION

However, fibers such as nylon and rayon which have been hitherto used are liable to bend in the formulations that include a great percentage of solid components such as waxes. Therefore, it was difficult to apply in a straight line along the eyelash, thereby not achieving a sufficient long lash effect, and in some cases, uniform make-up film could not be provided. Additionally, when the adhesiveness of the cosmetic composition is insufficient, an event of drop off of the fibers from the eyelashes over time may occur, resulting in problems also involving in long-lasting property of the make-up, in some cases. Hence, in order to achieve a sufficient long lash effect, increase in the amount of the fibers to be blended, or thickening of the fibers may be envisaged. However, increase of the amount or thickening of the fibers result in loss of smooth feel upon use, and any cosmetic composition for eyelashes could be obtained which is satisfactory in terms of the uniformity of the make-up film and long-lasting property of the make-up effects.

Accordingly, the present inventors elaborately investigated in order to solve the problem as described above, and consequently found that a cosmetic composition for eyelashes which is excellent in make-up effects (long lash effect) such as making the eyelashes appear longer and emphasizing eyes, exhibiting high long-lasting property of the make-up effects, having favorable usability, providing a uniform make-up film, and also having satisfactory stability can be obtained by making a cosmetic composition for eyelashes include: a component (A), polypropylene fibers having the thickness of 0.1 to 12 denier, and the length of 0.1 to 3 mm; and a component (B) an oil soluble resin. These findings have led to the completion of the present invention.

In brief, the invention relates to a cosmetic composition for eyelashes comprising a component (A), polypropylene fibers having the thickness of 0.1 to 12 denier, and the length of 0.1 to 3 mm; and a component (B), an oil soluble resin.

DESCRIPTION OF THE PREFERRED EMBODIMENTS

The present invention is explained in more detail below.

The polypropylene fibers having the thickness of 0.1 to 12 denier, and the length of 0.1 to 3 mm used as a component (A) in the cosmetic composition for eyelashes of the invention are synthetic fibers made from a propylene polymer into a fibrous stricture, having the thickness of 0.1 to 12 denier (hereinafter, merely indicated as "D"), and preferably 0.5 to 10 D. When the thickness is less than 0.1 D, satisfactory make-up effects such as making the eyelashes appear thicker and emphasizing the eyes may not be achieved, whilst when the thickness is greater than 12 D, satisfactory usability and formation of a uniform make-up film may not be achieved. In addition, the length of the polypropylene fibers is 0.1 to 3 mm, and preferably 0.5 to 2 mm. When the length is less than 0.1 mm, satisfactory make-up effects such as making the eyelashes appear longer and emphasizing the eyes may not be achieved, whilst when the length is greater than 3 mm, satisfactory usability and formation of a uniform make-up film may not be achieved.

The polypropylene fibers used in the invention as the component (A) may be those that had been subjected to a treatment with any one of general oil solutions, silicone oil, fluorine compounds, surfactants, powder of silica and the like, as needed. In particular, fibers of which surface was treated with silica or a fluorine compound are most preferred in light of dispersibility, stability and uniformity of the make-up film. Process for treating the surface of the fibers with silica is not particularly limited, but, for example, a process in which colloidal silica dispersed in water and fibers are admixed followed by filtration and drying is included. The fluorine compound for treating the surface of the fibers is not particularly limited as long as water repellency and oil repellency are accomplished through the treatment of fibers therewith. In particular, an ester containing a perfluoroalkyl group, perfluoroalkylsilane, perfluoro polyether, or a polymer containing a perfluoroalkyl group is preferably used.

Examples of the ester containing a perfluoroalkyl group include esters containing a perfluoroalkyl group represented by the following general formula (1)

[formula 1]

$$(RfC_mH_{2m}O)_yPO(OM)_{3-y} \qquad (1)$$

wherein Rf represents a perfluoroalkyl group or a perfluorooxyalkyl group having 3 to 21 carbon atoms, which may be straight chained or branched, and may have a single chain length or mixed chain lengths; m represents an integer number of 1 to 12; y represents a number of 1 to 3; and M may be the same or different, and represents hydrogen, alkali metal, ammonium, substituted ammonium or the like. Examples thereof include e.g., compounds having a perfluoroalkyl group such as perfluoroalkyl phosphate ester•diethanolamine salts, and diheptadecafluorodecyl phosphate, and specific example thereof includes e.g., Asahi guard AG-530 (manufactured by Asahi Glass Co., Ltd.).

Examples of the perfluoroalkylsilane include perfluoroalkylsilane represented by the following general formula (2)

[formula 2]

$$[C_aF_{2a+1}(CH_2)b]_cSiX_{4-c} \quad (2)$$

wherein a represents an integer number of 1 to 12; b represents an integer number of 1 to 5; c represents an integer number of 1 to 3; and X may be the same or different, and represents an alkoxy group, a halogen atom or an alkyl group, however, those having all the X being an alkyl group together are excluded. Specific examples include e.g., LS-160, LS-360, LS-912, LS-1080, LS-1090 and LS-1465 (manufactured by Shin-Etsu Chemical Co., Ltd.), and XC95-418, XC95-466, XC95-467, XC95-468, XC95-469, XC95-470, XC95-471 and XC95-472 (manufactured by Toshiba Silicone Co., Ltd.).

Examples of the perfluoro polyether include perfluoro perfluoro polyether represented by the following general formula (3)

[formula 3]

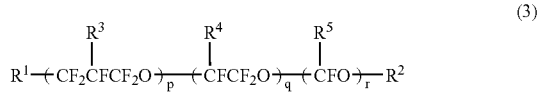

wherein $R^1$, $R^2$, $R^3$, $R^4$ and $R^5$ may be the same or different, and each represent a fluorine atom, a perfluoroalkyl group or an oxyperfluoroalkyl group; and p, q, and r represent an integer number of equal to or greater than 0, that give the molecular weight of 500 to 100,000, however that p, q, and r should not be defined as p=q=r=0. Specific examples thereof include e.g., FOMBLIN HC-04, FOMBLIN HC-25 and FOMBLIN HC—R (manufactured by AUSIMONT), and DEMNUMS-20, DEMNUMS-65, DEMNUM S-100 and DEMNUMS-200 (manufactured by Daikin Industries, Ltd.), and the like.

Examples of the polymer having a perfluoroalkyl group include e.g., single polymers of acrylate or methacrylate having a perfluoroalkyl group; copolymers of acrylate or methacrylate having a perfluoroalkyl group with a polymerizable compound such as an acrylate ester, maleic anhydride, chloroprene, butadiene or methyl vinyl ketone; polymers or copolymers of a polymerizable compound having a perfluoroalkyl group represented by the following general formulae (4) to (6)

[formula 4]

(4)

[formula 5]

$$H(CF_2)_{10}CH_2OCOCH=CH_2 \quad (5)$$

[formula 6]

$$CF_2Cl(CF_2)10CH_2OCOC(CH_3)=CH_2 \quad (6)$$

or copolymers of these polymers with one or two or more polymerizable compounds not having a perfluoroalkyl group such as vinyl chloride, vinyl acetate, vinyl fluoride, ethylene, halogenated vinylidene, acrylonitrile, styrene, α-methylstyrene, p-methylstyrene, acrylamide, methacrylamide, diacetone acrylamide, methylolated diacetone acrylamide, N-methylol acrylamide, vinyl alkyl ether, halogenated alkyl vinyl ether, isoprene and glycidyl acrylate; and the like.

Process for treating the fibers with a fluorine compound is not particularly limited, but any known method may be employed. For example, when a perfluoroalkyl phosphate ester•diethanolamine salt is used as a fluorine compound, water is added to a kind of fibers or a mixture of two or more kinds of fibers to give a slurry form. On the other hand, a perfluoroalkyl phosphate ester•diethanolamine salt is added to water followed by stirring to give the concentration of 0.1 to 10% by weight (hereinafter, merely indicated as "%"). The latter mixture is gradually poured into the former slurry followed by mixing. Thereafter, thus resulting mixture is acidified and left to stand at an ambient temperature or a high temperature, followed by washing, filtration and drying. Further, in the scope not to compromise the effect of the invention, a pretreatment or a simultaneous treatment may be carried out with any other coating agent such as silicone, a higher fatty acid, a higher alcohol, an ester or wax except for the fluorine compound. Percentage of the surface, which may be treated, of the polypropylene fibers of the component (A) used in the invention is preferably 0.1 to 20% in light of the dispersibility in the cosmetic composition.

Amount to be blended of the polypropylene fibers of the component (A) used in the cosmetic composition for eyelashes of the invention is preferably 0.1 to 10%, and more preferably 0.5 to 5%. When the amount is within this range, a satisfactory cosmetic composition can be obtained in respect of make-up effects such as making the eyelashes appear longer and emphasizing the eyes, as well as uniformity of the make-up film.

The oil soluble resin of the component (B) used in the cosmetic composition for eyelashes of the invention is not particularly limited, but any one may be used as long as it is soluble in oil and forms a film when it is turned into a make-up film. Specific examples thereof include terpene-based resins such as pentaerythrityl rosinate, trimethylsiloxy silicate, candelilla resins (candelilla resin herein refers to a resin component obtained by fractional extraction of candelilla wax with an organic solvent, preferably containing the resin component in a ratio of 65% or greater and more preferably 85% or greater, and having the softening point of preferably 35 to 55° C.), silicone grafted acrylic resin, vinyl acetate-based resins, polyvinylisobutyl ether, polyisobutylene and the like, which may be used alone or in combination of two or more of the same. Among these resins, terpene-based resins and candelilla resins are particularly preferred in light of make-up effects such as making the eyelashes appear longer and emphasizing the eyes, as well as long-lasting property of the make-up effects. In addition, by using a candelilla resin, adhesiveness between the polypropylene fibers and eyelashes can be further enhanced.

Amount to be blended of the oil soluble resin of the component (B) used in the cosmetic composition for eyelashes of the invention is preferably 0.5 to 20%, and more preferably 1 to 15%. When the amount is within this range, a satisfactory cosmetic composition can be obtained in terms of the long-lasting property of make-up effects such as making the eyelashes appear longer and emphasizing the eyes.

In the cosmetic composition for eyelashes of the invention may be blended any of the ingredients generally used in cosmetic compositions within the range not to compromise the effect of the invention, such as for example: a film forming polymer emulsion having an effect to improve the adhesiveness, long-lasting property and stability; a powdery ingredient aiming at adjusting the feel or coloring; an oily ingredient as a base material or an emollient ingredient; an aqueous ingredient as a moisturizing agent or powder dispersing agent; a surfactant for powder dispersion and adjustment of the sensory feel; an ultraviolet ray absorbing agent; a moisturizing agent; a film forming water soluble resin such as polyvinyl alcohol, polyvinyl pyrrolidone, vinyl pyrrolidone•vinyl acetate copolymer; a color deterioration preventive agent; an oxidation inhibitor; a deforming agent; a cosmetic ingredient; an antiseptic agent; flavor; and the like, ad libitum.

The film forming polymer emulsion that can be used may be any one without particular limitation which has been used in general cosmetics as a film-forming polymer emulsion in which a polymer compound is dispersed in an aqueous medium. Examples thereof include e.g., alkyl (meth)acrylate polymer emulsions, alkyl (meth)acrylate copolymer emulsions, (meth)acrylate•alkyl (meth) acrylate copolymer emulsions, alkyl (meth) acrylate•styrene copolymer emulsions, vinyl acetate polymer emulsions, copolymer emulsions containing vinyl acetate, vinyl pyrrolidone•styrene copolymer emulsions, polymer emulsions containing silicone, copolymer emulsions containing silicone and the like. These polymer emulsions may be used alone or in combination of two or more kinds as needed.

Examples of the oily ingredient include hydrocarbons, fats and oils, waxes, hydrogenatedoils, ester oils, fatty acids, higher alcohols, silicone oils, fluorinated oils, lanolin derivatives, oily gelatinizing agents and the like, irrespective of the origin such as animal oil, plant oil or synthetic oil, and the characteristic states such as solid oil, semisolid oil, liquid oil or volatile oil or the like. Specific examples include hydrocarbons such as liquid paraffin, squalane, vaseline, polybutene, paraffin wax, ceresin wax, microcrystalline wax, polyethylene wax, ethylene•propylene copolymers, montan wax and Fischer-Tropsch wax; fats and oils such as vegetable tallow, olive oil, castor oil, mink oil and macadamia nut oil; waxes such as bees wax, carnauba wax, candelilla wax, jojoba oil and whale wax; esters such as diisostearyl malate, cetyl isooctanate, isopropyl myristate, isopropyl palmitate, octyldodecyl myristate, glyceryl trioctanate, polyglyceryl diisostearate, diglyceryl triisostearate, glyceryl tribehenate, neopentylglycol dioctanate, cholesterol fatty acid esters and di(cholesteryl•behenyl•octyldodecyl) N-lauroyl-L-glutamate; fatty acids such as stearic acid, lauric acid, myristic acid, behenic acid, isostearic acid and oleic acid; higher alcohols such as stearyl alcohol, cetyl alcohol, lauryl alcohol, oleyl alcohol, isostearyl alcohol and behenyl alcohol; silicones such as dimethylpolysiloxane, methylphenylpolysiloxane, decamethylcyclopentasiloxane, octamethylcyclotetrasiloxane, polyether modified organopolysiloxane, polyoxyalkylene alkylmethylpolysiloxane•methylpolysiloxane copolymers, alkoxy modified polysiloxane and fluorine modified organopolysiloxane; fluorinated oils such as perfluorodecane, perfluorooctane and perfluoro polyether; lanolin derivatives such as lanolin, acetic acid lanolin, lanolin fatty isopropyl and lanolin alcohol; oily gelatinizing agents such as dextrin fatty acid esters, sucrose fatty acid esters, starch fatty acid esters, 12-hydroxystearic acid, aluminum isostearate and calcium stearate; and the like.

The powdery ingredient is not particularly limited in terms of: the shape such as plate-shaped, spindle-shaped or needle shaped; the particle size; the particle structure such as porous or nonporous; and the like, but the examples thereof may include inorganic powder, photoluminescent powder, organic powder, pigment powder, composite powder and the like. Specific examples include inorganic powder such as iron blue, ultramarines, red iron oxide, yellow iron oxide, black iron oxide, titanium dioxide, zinc oxide, aluminum oxide, cerium oxide, silicon dioxide, magnesium oxide, zirconium oxide, magnesium carbonate, calcium carbonate, chromium oxide, chromium hydroxide, carbon black, aluminum silicate, magnesium silicate, aluminum magnesium silicate, mica, synthetic mica, synthetic sericite, sericite, talc, kaolin, silica, silicon carbide, barium sulfate, bentonite, smectite and boron nitride; photoluminescent powder such as bismuth oxychloride, titanated mica, mica coated with iron oxide, titanated mica coated with iron oxide, titanated mica treated with an organic pigment and aluminum powder; organic powder such as magnesium stearate, zinc stearate, N-acyllysine and nylon; pigment powder such as organic coal-tar dyes and lake colorants of an organic pigment; composite powder such as titanated mica coated with particulate titanium dioxide, titanated mica coated with particulate zinc oxide, titanated mica coated with barium sulfate, silica containing titanium dioxide and silica containing zinc oxide; polyethylene terephthalate•aluminum•epoxy laminated powder, polyethylene terephthalate•polyolefin laminated film powder, polyethylene terephthalate•polymethylmethacrylate laminated film powder; and the like. These may be used alone or in combination of two or more kinds. In addition, the powder which can be used may be any complex of one or two or more kinds thereof, and may be subjected to a surface treatment by a known method using a fluorinated compound, a silicone-based oil solution, a metal soap, a wax, a surfactant, a fat or an oil, a hydrocarbon or the like.

The aqueous ingredient may be anyone as long as it is a component that is soluble in water, and examples thereof include e.g., alcohols such as ethyl alcohol and isopropyl alcohol; glycols such as propylene glycol, 1,3-butylene glycol, dipropylene glycol and polyethylene glycol; glycerols such as glycerin, diglycerin and polyglycerin; saccharides such as sorbitol, maltitol, sucrose, starch sugar and lactitol; water soluble polymers such as guar gum, sodium chondroitin sulfate, sodiumhyaluronate, gum arabic, sodium alginate, carrageenan methyl cellulose, hydroxyethyl cellulose, carboxymethyl cellulose, carboxyvinyl polymer, polyvinyl alcohol, polyvinyl pyrrolidone and sodium polyacrylate; salts such as sodium chloride, magnesium chloride and sodium lactate; plant extracts such as aloe vera, hamamelis virginiana, cucumber, lemon, lavender and rose; and water.

The surfactant which can be used may be any surfactant used in general cosmetics, including nonionic surfactants, anionic surfactants, cationic surfactants, amphoteric surfactants and the like. Examples of the nonionic surfactant include e.g., glycerin fatty acid esters and the alkylene glycol addition products of the same, polyglycerin fatty acid esters and the alkylene glycol addition products of the same, propylene glycol fatty acid esters and the alkylene glycol addition products of the same, sorbitan fatty acid esters and the alkylene glycol addition products of the same, fatty acid esters of sorbitol and the alkylene glycol addition products of the same, polyalkylene glycol fatty acid esters, sucrose fatty acid esters, polyoxyalkylene alkyl ether, glycerin alkyl ether, polyoxyethylene alkylphenyl ether, polyoxyethylene hydrogenated castor oil, alkylene glycol addition products of lanolin, polyoxyalkylene alkyl co-modified organopolysiloxane, polyether modified organopolysiloxane and the like. Examples of the anionic surfactant include e.g., inorganic or organic salts of a fatty acid such as stearic acid or lauric acid, alkyl benzene sulfates, alkyl sulfonates, a-olefin sulfonates, dialkyl sulfosuccinates, a-sulfonated fatty salts, acylmethyl taurine salts, N-methyl-N-alkyl taurine salts, polyoxyethylene alkyl ether sulfates, polyoxyethylene alkyl phenyl ether sulfates, alkyl phosphates, polyoxyethylene alkyl ether phosphates, polyoxyethylene alkylphenyl ether phosphates, N-acyl amino acid salts, N-acyl-N-alkyl amino acid salts, o-alkyl substituted malates, alkyl sulfosuccinates and the like. Examples of the cationic surfactant include e.g., alkylamine salts, polyamine and alkanol amine fatty acid derivatives, alkyl quaternary ammonium salts, cyclic quaternary ammonium salts, and the like. Examples of the amphoteric surfactant include those that are amino acid typed, and betaine typed carboxylic acid type, sulfate ester type, sulfonic acid type and phosphoric acid ester type, and those which can be used include ones referred to as being safe to the human body. Examples thereof include e.g., N,N-dimethyl-N-alkyl-N-carboxylmethyl ammonium betaine, N,N-dialkylamino alkylene carboxylic acid, N,N,N-trialkyl-N-sulfoalkylene ammonium betaine, N,N-dialkyl-N,N-bis(polyoxyethylene sulfate) ammonium betaine, 2-alkyl-1-hydroxyethyl-1-carboxymethyl imidazolium betaine, lecithin and the like.

Examples of the ultraviolet ray absorbing agent include e.g., those benzophenone-derivatives, PABA-derivatives, cinnamicacid-derivatives, and salicylic acid-derivatives, and 4-tert-butyl-4'-methoxy dibenzoylmethane, oxybenzone, and the like. Examples of the moisturizing agent include e.g., proteins, mucopolysaccharides, collagen, elastin, keratin and the like. Examples of the oxidation inhibitor include e.g., α-tocopherol, ascorbic acid and the like. Examples of the cosmetic ingredient include e.g., vitamins, antiphlogistics, herbal medicines and the like. Examples of the antiseptic agent include e.g., p-hydroxybenzoate esters, phenoxyethanol and the like.

The cosmetic composition for eyelashes according to the invention may be also adopted to any eye make-up cosmetic composition other than the eyelash cosmetic compositions, for example, eyebrow, and eye colors and eye liners. However, it is particularly preferably an eyelash cosmetic composition such as mascaras. Furthermore, examples of the formulation of the cosmetic composition of the invention include oily type and emulsion type. State of the cosmetic composition of the invention may be any of the cream state, gelled state, liquid state or the like, and among these, the gelled state is preferred. Such a cosmetic composition can be employed with any appearance of transparent, translucent or opaque.

EXAMPLES

The present invention is explained in detail by way of Examples below. These Examples do not anyhow limit the present invention.

Examples 1 to 5 and Comparative Examples 1 to 4: O/W type mascara

Mascaras formulated as shown in Table 1 were prepared, and subjected to sensory evaluation for make-up effects such as making the eyelashes appear longer and emphasizing the eyes, and long-lasting property of such make-up effects, easiness of the make-up upon application (usability and feel upon use) as well as the uniformity of the finished film. The results are also shown in Table 1, in combination.

TABLE 1

(%)

| | Example | | | | | Comparative Example | | | |
|---|---|---|---|---|---|---|---|---|---|
| No. Component | 1 | 2 | 3 | 4 | 5 | 1 | 2 | 3 | 4 |
| (1) Stearic acid | 3 | 3 | 3 | 3 | 3 | 3 | 3 | 3 | 3 |
| (2) Carnauba wax | 5 | 5 | 5 | 1 | 5 | 5 | 6 | 5 | 5 |
| (3) Candelilla resin*1 | 5 | 5 | 5 | 10 | 1 | 5 | — | 5 | 5 |
| (4) Cetyl alcohol | 1 | 1 | 1 | 1 | 1 | 1 | 1 | 1 | 1 |
| (5) Purified water | balance | balance | balance | balance | balance | balance | balance | balance | balance |
| (6) Triethanolamine | 1.5 | 1.5 | 1.5 | 1.5 | 1.5 | 1.5 | 1.5 | 1.5 | 1.5 |
| (7) Polypropylene fiber*2 | 2 | 0.5 | 5 | 2 | 2 | — | 2 | — | — |
| (8) Polypropylene fiber*3 | — | — | — | — | — | — | — | — | 2 |
| (9) Nylon fiber*4 | — | — | — | — | — | 2 | — | — | — |
| (10) Rayon fiber*5 | — | — | — | — | — | — | — | 2 | — |
| (11) Alkyl acrylate copolymer emulsion*6 | 40 | 40 | 40 | 40 | 40 | 40 | 40 | 40 | 40 |
| (12) Methyl p-hydroxybenzoate | 0.5 | 0.5 | 0.5 | 0.5 | 0.5 | 0.5 | 0.5 | 0.5 | 0.5 |
| (13) Chamomile extract | 0.1 | 0.1 | 0.1 | 0.1 | 0.1 | 0.1 | 0.1 | 0.1 | 0.1 |
| (14) Black iron oxide | 8 | 8 | 8 | 8 | 8 | 8 | 8 | 8 | 8 |
| (15) Silica*7 | 5 | 5 | 5 | 5 | 5 | 5 | 5 | 5 | 5 |
| Items of evaluation and Results of determination | | | | | | | | | |
| a Make-up effect (long lash effect) | ⊚ | ○ | ⊚ | ⊚ | ⊚ | Δ | ○ | Δ | ○ |
| b Long-lasting of make-up effect | ⊚ | ⊚ | ⊚ | ⊚ | ○ | ○ | X | ○ | Δ |
| c Usability of making-up | ⊚ | ⊚ | ○ | ○ | ⊚ | ○ | Δ | ○ | X |
| d Uniformity of finished film | ⊚ | ⊚ | ○ | ⊚ | ⊚ | Δ | Δ | Δ | Δ |

*1: softening point 47 to 48° C.
*2: 6 D, 1 mm, treated with 0.5% silica
*3: 20 D, 4 mm, treated with 0.5% silica
*4: 6 D, 1 mm, untreated
*5: 6 D, 1 mm, untreated
*6: solid content 40%
*7: SYLYSIA 550 (manufactured by Fuji Silysia Chemical Ltd.)

(Process for Production)

Examples 1 to 5 and Comparative Examples 1 to 4
A. Components (5) to (15) are admixed to be homogenous, and heated to 80° C.
B. Components (1) to (4) are heated and melted (80° C.).
C. B is added to A to permit emulsification.
D. C is packed into a vessel to give a product.

(Method of Evaluation)

Ten sensory testing panels evaluated each sample for the following items a to d with (1) absolute evaluation standards of 7 grades, and the mean value of the score for every each sample was determined using (2) determination criteria of 4 grades. In connection with the evaluation item b, the sample was applied to the eyelashes, and the panels lead a normal life. Then evaluation was made for the make-up effect 12 hours thereafter.

(Items for Evaluation)

a. make-up effects (long lash effect)
b. long-lasting of the make-up effect
C. usability of the make-up
d. uniformity of the finished film (1) Absolute evaluation standards (Score): (Evaluation)

6: very good
   5: good
   4: rather good
   3: normal
   2: rather bad
   1: bad
   0: very bad (2) Determination criteria of 4 grades beyond 5 points:extremely favorable: ⊚
beyond 3 points and 5 points or less: favorable: ○
beyond 2 points and 3 points or less: rather unfavorable: △
2 points or less: unfavorable: ×

As is clear from the results shown in Table 1, it is revealed that mascaras of Examples 1 to 5 that are the products of the present invention have far more excellent characteristics in all terms of: make-up effects such as making the eyelashes appear longer and emphasizing the eyes, and long-lasting property of such effects, usability of the make-up as well as the uniformity of the finished film, in comparison with mascaras of the Comparative Examples 1 to 4.

On the other hand, in Comparative Example 1 without blending the polypropylene fibers but with blending nylon fibers, and in Comparative Example 3 also without blending the polypropylene fibers but with blending rayon fibers, satisfactory products were not obtained in terms of make-up effects such as making the eyelashes longer and emphasizing the eyes, as well as uniformity of the finished film. Further, satisfactory products were not also obtained: in terms of the usability of the make-up and the uniformity of the finished film in Comparative Example 4 in which thick and long polypropylene fibers were used; and in terms of long-lasting make-up effects such as making the eyelashes longer and emphasizing the eyes, and the usability of the make-up as well as the uniformity of the finished film in Comparative Example 2 without blending any oil soluble resin component.

Example 6

Oil-Based Mascara

| (Component) | (%) |
|---|---|
| (1) Pentaerythrityl rosinate | 9 |
| (2) Polyisobutylene *8 | 1 |
| (3) Light liquid isoparaffin | 53.4 |
| (4) Polyethylene wax | 10 |
| (5) Dextrin fatty acid ester | 5 |
| (6) Polypropylene fiber *9 | 10 |
| (7) Red iron oxide | 5 |
| (8) Talc *10 | 5 |
| (9) Nasturtium officinale extract | 0.5 |

-continued

| (Component) | (%) |
|---|---|
| (10) Phenoxy ethanol | 1 |
| (11) Flavor | 0.1 |

*8: Molecular weight 100,000
*9: 1 D, 2 mm, treated with 5% perfluoroalkyl phosphate ester · diethanolamine salt
*10: treated with 2% dimethylpolysiloxane (Process for Production)

A. Components (1) to (5) are heated and melted, and thereto are added components (6) to (11) followed by admixing to be homogenous.

B. A is packed into a vessel to give a product.

The mascara obtained according to the process as described above was excellent in terms of: make-up effects such as making the eyelashes appear longer and emphasizing the eyes, long-lasting of such make-up effects, usability of the make-up, and the uniformity of the make-up film.

Example 7

W/O Type Mascara

| (Component) | (%) |
|---|---|
| (1) Trimethylsiloxy silicate | 20 |
| (2) Decamethylcyclopentasiloxane | 41.4 |
| (3) Polyoxyethylene · methylpolysiloxane copolymer *11 | 5 |
| (4) Tocopherol | 0.5 |
| (5) Ethyl parahydroxybenzoate | 1 |
| (6) Purified water | 15 |
| (7) Polypropylene fiber *12 | 1 |
| (8) Polypropylene fiber *13 | 1 |
| (9) Titanium · titanium dioxide sinter *14 | 10 |
| (10) Titanated mica coated with red iron oxide | 5 |
| (11) Polyvinyl pyrrolidone | 0.1 |

*11: silicone KF-6017 (manufactured by Shin-Etsu Chemical Co., Ltd.)
*12: 10 D, 3 mm, untreated
*13: 6 D, 1 mm, untreated
*14: Tilack D (manufactured by AKŌ KASEI CO., LTD.)

(Process for Production)

A. Components (1) to (5) are heated and melted, and thereto are added components (6) to (11) followed by admixing to be homogenous.

B. A is packed into a vessel to give a product.

The mascara obtained according to the process as described above was excellent in terms of: make-up effects such as making the eyelashes appear longer and emphasizing the eyes, long-lasting of such make-up effects, usability of the make-up, and the uniformity of the make-up film.

Example 8

Oil-Based Eyebrow

| (Component) | (%) |
|---|---|
| (1) Polyisobutylene *15 | 2 |
| (2) Light liquid isoparaffin | 70.4 |
| (3) Liquid paraffin | 2 |

-continued

| (Component) | (%) |
|---|---|
| (4) Polypropylene fiber *16 | 15 |
| (5) Nylon fiber *17 | 0.1 |
| (6) Silica dimethyl silylate *18 | 5 |
| (7) *Rosmarinus officinalis* leaf extract | 0.5 |
| (8) Ethanol | 5 |

*15: molecular weight 50,000
*16: 0.5 D, 0.5 mm, untreated
*17: 0.5 D, 0.5 mm, untreated
*18: AEROSIL R972 (manufactured by NIPPON AEROSIL CO., LTD.)

(Process for Production)

A. Components (1) to (3) are heated and melted, and thereto are added components (4) to (8) followed by admixing to be homogenous.

B. A is packed into a vessel to give a product.

The eyebrow obtained according to the process as described above was excellent in terms of: make-up effects such as making the eyebrows, which are application sites, fix up and be highlighted, long-lasting of such make-up effects, usability of the make-up, and the uniformity of the make-up film.

Example 9

Oil-Based Mascara

| (Component) | (%) |
|---|---|
| (1) Pentaerythrityl rosinate | 9 |
| (2) Candelilla resin *19 | 1 |
| (3) Light liquid isoparaffin | 53.4 |
| (4) Polyethylene wax | 10 |
| (5) Dextrin fatty acid ester | 5 |
| (6) Polypropylene fiber *9 | 10 |
| (7) Titanium · titanium dioxide sinter *14 | 5 |
| (8) Talc *10 | 5 |
| (9) Nasturtium officinale extract | 0.5 |
| (10) Phenoxy ethanol | 1 |
| (11) Flavor | 0.1 |

*19: Softening point 40 to 41° C.

(Process for Production)

A. Components (1) to (5) are heated and melted, and thereto are added components (6) to (11) followed by admixing to be homogenous.

B. A is packed into a vessel to give a product.

The mascara obtained according to the process as described above was excellent in terms of: make-up effects such as making the eyelashes appear longer and emphasizing the eyes, long-lasting of such make-up effects, usability of the make-up, and the uniformity of the make-up film.

Accordingly, the cosmetic composition for eyelashes of the present invention is excellent in make-up effects such as making the eyelashes appear longer and emphasizing the eyes, and in long-lasting property of such make-up effects, and in terms of usability and feel upon use, further, it exhibits easiness of the make-up as well as excellent uniformity of the make-up film.

What is claimed is:

1. A cosmetic composition for eyelashes comprising: polypropylene fibers having a thickness of from 0.1 denier to 12 denier, and a length of from 0.1 mm to 3 mm, wherein a surface of the polypropylene fibers is treated with silica; and an oil soluble resin.

2. The cosmetic composition for eyelashes according to claim 1, wherein the polypropylene fibers have a length of from 0.5 mm to 3 mm.

3. The cosmetic composition for eyelashes according to claim 1, wherein the polypropylene fibers are present in an amount ranging from 0.1 wt. % to 10 wt. %.

4. The cosmetic composition for eyelashes according to claim 1, wherein the polypropylene fibers are present in an amount ranging from 0.5 wt. % to 5 wt. %.

5. The cosmetic composition for eyelashes according to claim 1, wherein the oil soluble resin is present in an amount ranging from 0.5 wt. % to 20 wt. %.

6. The cosmetic composition for eyelashes according to claim 1, wherein the oil soluble resin is present in an amount ranging from 1 wt. % to 15 wt. %.

7. The cosmetic composition for eyelashes according to claim 1, wherein the oil soluble resin is one or more oil soluble resins selected from the group consisting of candelilla resin obtained from fractionation and having a softening point of from 35° C. to 55° C., pentaerythrityl rosinate, trimethylsiloxy silicate, decamethylcyclopentasiloxane, polyisobutylene and polyvinylisobuty ether.

8. The cosmetic composition for eyelashes according to claim 1, wherein the oil soluble resin comprises a candelilla resin obtained from fractionation and having a softening point of from 35° C. to 55° C.

9. The cosmetic composition for eyelashes according to claim 1, wherein the oil soluble resin comprises a candelilla resin obtained from fractionation and having a softening point of from 40° C. to 48° C.

10. The cosmetic composition for eyelashes according to claim 1, wherein the oil soluble resin comprises a candelilla resin obtained from fractionation and having a softening point of from 40° C. to 41° C.

11. The cosmetic composition for eyelashes according to claim 1, wherein the oil soluble resin comprises a candelilla resin obtained from fractionation and having a softening point of from 47° C. to 48° C.

12. A cosmetic composition for eyelashes comprising:
0.5 wt. % to 5 wt. % of polypropylene fibers having a thickness of from 0.1 denier to 12 denier, and a length of from 0.1 mm to 3 mm; and
1 wt. % to 15 wt. % of an oil soluble resin, wherein the oil soluble resin is one or more oil soluble resins selected from the group consisting of candelilla resin obtained from fractionation and having a softening point of from 35° C. to 55° C., pentaerythrityl rosinate, trimethylsiloxy silicate, decamethylcyclopentasiloxane, polyisobutylene and polyvinylisobuty ether.

13. The cosmetic composition for eyelashes according to claim 12, wherein the polypropylene fibers have a length of from 0.5 mm to 3 mm.

14. The cosmetic composition for eyelashes according to claim 12, wherein the oil soluble resin comprises a candelilla resin obtained from fractionation and having a softening point of from 35° C. to 55° C.

15. The cosmetic composition for eyelashes according to claim 12, wherein the oil soluble resin comprises a candelilla resin obtained from fractionation and having a softening point of from 40° C. to 48° C.

16. The cosmetic composition for eyelashes according to claim 12, wherein the oil soluble resin comprises a candelilla resin obtained from fractionation and having a softening point of from 40° C. to 41° C.

17. The cosmetic composition for eyelashes according to claim 12, wherein the oil soluble resin comprises a candelilla resin obtained from fractionation and having a softening point of from 47° C. to 48° C.

18. A cosmetic composition for eyelashes comprising:
0.5 wt. % to 5 wt. % of polypropylene fibers having a thickness of from 0.1 denier to 12 denier, and a length of from 0.1 mm to 3 mm, wherein a surface of the polypropylene fibers is treated with 5 wt. % to 10 wt. % of a perfluoroalkylsilane compound according to the following general formula (2):

  (2)

wherein a is 4, b is 2, c is 1 and X is -OCH$_2$CH$_3$; and 1 wt. % to 15 wt. % of an oil soluble resin, wherein the oil soluble resin is a candelilla resin obtained from fractionation and having a softening point of from 35° C. to 55° C.

19. The cosmetic composition for eyelashes according to claim 18, wherein the polypropylene fibers have a length of from 0.5 mm to 3 mm.

20. The cosmetic composition for eyelashes according to claim 18, wherein the oil soluble resin comprises a candelilla resin obtained from fractionation and having a softening point of from 40° C. to 48° C.

21. The cosmetic composition for eyelashes according to claim 18, wherein the oil soluble resin comprises a candelilla resin obtained from fractionation and having a softening point of from 40° C. to 41° C.

22. The cosmetic composition for eyelashes according to claim 18, wherein the oil soluble resin comprises a candelilla resin obtained from fractionation and having a softening point of from 47° C. to 48° C.

* * * * *